United States Patent [19]
Gorski

[11] Patent Number: 5,837,447
[45] Date of Patent: Nov. 17, 1998

[54] MONITORING AN IMMUNE RESPONSE BY ANALYSIS OF AMPLIFIED IMMUNOGLOBULIN OR T-CELL-RECEPTOR NUCLEIC ACID

[75] Inventor: Jack Gorski, Mukwonago, Wis.

[73] Assignee: Blood Center Research Foundation, Inc., The, Milwaukee, Wis.

[21] Appl. No.: 229,528

[22] Filed: Apr. 19, 1994

Related U.S. Application Data

[63] Continuation-in-part of Ser. No. 868,569, Apr. 15, 1992, abandoned.

[51] Int. Cl.$^6$ ............................... C12Q 1/68; C12P 19/34
[52] U.S. Cl. ............................................... 435/6; 435/91.2
[58] Field of Search ........................ 435/6, 91.2; 935/78

[56] References Cited

U.S. PATENT DOCUMENTS

| | | | |
|---|---|---|---|
| 4,717,653 | 1/1988 | Webster, Jr. ................................. | 435/5 |
| 5,336,598 | 8/1994 | Kotzin et al. ........................... | 435/7.24 |
| 5,635,354 | 6/1997 | Kourilsky et al. ........................... | 435/6 |

OTHER PUBLICATIONS

Gorski: et al., *J. Immunol.* 152, 5109–5119 (1994).
Hingorani et al., *J. Immunol.* 151(10), 5762–5769 (1993).
Pannetier et al., PNAS 90, 4319–4323 (1993).
Cochet et al., *Eur. J. Immunol.* 22, 2639–2647 (1992 Oct.).
Bangs et al., *J. Immunol.* 146(6), 1996–2004 (1991).
Hayzer et al., *Biochem. J.* 245, 691–697 (1987).
Brisco et al., *Br. J. Haematol.* 75, 163–167 (1990).
Yamada et al., *J. Exp. Med.* 173, 395–407 (1991 Feb.).
Goudie, *J. Pathol.* 158, 261–265 (1989).
Choi et al., *PNAS* 86, 8947–8945 (1989).
Berger & Kimmel, *Guide to Molecular Cloning Techniques*, Academic Press, Inc., Orlando, 1987, pp. 66–73.
Marks et al., *Eur. J. Immunol.* 21, 985–991 (1991).
Dallman et al., *J. Exp. Med.* 173, 79–87 (1991).
Mueller et al., *J. Exp. Med.* 167, 1124–1136 (1988).
Reynolds et al., *Cell* 50, 107–117 (1987).

*Primary Examiner*—Kenneth R. Horlick
*Attorney, Agent, or Firm*—Foley & Lardner

[57] ABSTRACT

An approach to monitoring immune responses relies on determining the range of sizes of amplified DNAs which code for the CDR3 regions of Ig or TcR molecules of one or more classes or families. Typically the relative quantity of DNAs corresponding to different CDR3 regions of the Ig or TcR molecules of a class is also determined. The progress of an immune response is followed by making these determinations at different times.

27 Claims, 5 Drawing Sheets

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:1:

```
CTAAACCTGA   GCTCTCTGGA   G                                    21
```

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:2:

```
GCTTCTACAT   CTGCAGTGC                                         19
```

( 2 ) INFORMATION FOR SEQ ID NO:3:

(i) SEQUENCE CHARACTERISTICS:
   (A) LENGTH: 18 base pairs
   (B) TYPE: nucleic acid
   (C) STRANDEDNESS: single
   (D) TOPOLOGY: linear (ii) MOLECULE TYPE: Other nucleic acid;
   (A) DESCRIPTION: Synthetic DNA oligonucleotide (xi) SEQUENCE DESCRIPTION: SEQ ID NO:3:

CTGGAGTCCG CCAGCACC                    18

(2) INFORMATION FOR SEQ ID NO:4:

(i) SEQUENCE CHARACTERISTICS:
   (A) LENGTH: 18 base pairs
   (B) TYPE: nucleic acid
   (C) STRANDEDNESS: single
   (D) TOPOLOGY: linear (ii) MOLECULE TYPE: Other nucleic acid;
   (A) DESCRIPTION: Synthetic DNA oligonucleotide (xi) SEQUENCE DESCRIPTION: SEQ ID NO:4:

GCAACATGAG CCCTGAAG                    18

(2) INFORMATION FOR SEQ ID NO:5:

(i) SEQUENCE CHARACTERISTICS:
   (A) LENGTH: 22 base pairs
   (B) TYPE: nucleic acid
   (C) STRANDEDNESS: single
   (D) TOPOLOGY: linear (ii) MOLECULE TYPE: Other nucleic acid;
   (A) DESCRIPTION: Synthetic DNA oligonucleotide (xi) SEQUENCE DESCRIPTION: SEQ ID NO:5:

GATGAATGTG AGCACCTTGG AG               22

(2) INFORMATION FOR SEQ ID NO:6:

(i) SEQUENCE CHARACTERISTICS:
   (A) LENGTH: 22 base pairs
   (B) TYPE: nucleic acid
   (C) STRANDEDNESS: single
   (D) TOPOLOGY: linear (ii) MOLECULE TYPE: Other nucleic acid;
   (A) DESCRIPTION: Synthetic DNA oligonucleotide (xi) SEQUENCE DESCRIPTION: SEQ ID NO:6:

GCTGAATGTG AACGCCTTGT TG               22

(2) INFORMATION FOR SEQ ID NO:7:

(i) SEQUENCE CHARACTERISTICS:
   (A) LENGTH: 17 base pairs
   (B) TYPE: nucleic acid
   (C) STRANDEDNESS: single
   (D) TOPOLOGY: linear (ii) MOLECULE TYPE: Other nucleic acid;
   (A) DESCRIPTION: Synthetic DNA oligonucleotide (xi) SEQUENCE DESCRIPTION: SEQ ID NO:7:

GATCCAGCGC ACACAGC                     17

(2) INFORMATION FOR SEQ ID NO:8:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: linear ( i i ) MOLECULE TYPE: Other nucleic acid;
 ( A ) DESCRIPTION: Synthetic DNA oligonucleotide ( x i ) SEQUENCE DESCRIPTION: SEQ ID NO:8:

GATCCAGCGC ACAGAGC                                          17

( 2 ) INFORMATION FOR SEQ ID NO:9:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: Other nucleic acid;
  ( A ) DESCRIPTION: Synthetic DNA oligonucleotide ( x i ) SEQUENCE DESCRIPTION: SEQ ID NO:9:

CCTGAATGCC CCAACAGC                                         18

( 2 ) INFORMATION FOR SEQ ID NO:10:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: Other nucleic acid;
  ( A ) DESCRIPTION: Synthetic DNA oligonucleotide ( x i ) SEQUENCE DESCRIPTION: SEQ ID NO:10:

CCAGCCCTCA GAACCCAG                                         18

( 2 ) INFORMATION FOR SEQ ID NO:11:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: Other nucleic acid;
  ( A ) DESCRIPTION: Synthetic DNA oligonucleotide ( x i ) SEQUENCE DESCRIPTION: SEQ ID NO:11:

CCCTGGAGCT TGGTGACTCT GC                                    22

( 2 ) INFORMATION FOR SEQ ID NO:12:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: Other nucleic acid;
  ( A ) DESCRIPTION: Synthetic DNA oligonucleotide ( x i ) SEQUENCE DESCRIPTION: SEQ ID NO:12:

CCAGTCCACG GAGTCAGG                                         18

( 2 ) INFORMATION FOR SEQ ID NO:13:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide ( x i ) SEQUENCE DESCRIPTION: SEQ ID NO:13:

CCCTGGAGTC TGCCAGGC                18

( 2 ) INFORMATION FOR SEQ ID NO:14:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide ( x i ) SEQUENCE DESCRIPTION: SEQ ID NO:14:

CTCTGGAGTC CGCTACCAG               19

( 2 ) INFORMATION FOR SEQ ID NO:15:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide ( x i ) SEQUENCE DESCRIPTION: SEQ ID NO:15:

GCTCAGGCTG CTGTCGGCTG C            21

( 2 ) INFORMATION FOR SEQ ID NO:16:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide ( x i ) SEQUENCE DESCRIPTION: SEQ ID NO:16:

GTCTCTCGAA AAGAGAAGAG G            21

( 2 ) INFORMATION FOR SEQ ID NO:17:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide ( x i ) SEQUENCE DESCRIPTION: SEQ ID NO:17:

CCCTAGAGTC TGCCATCC                18

( 2 ) INFORMATION FOR SEQ ID NO:18:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: Other nucleic acid;
  ( A ) DESCRIPTION: Synthetic DNA oligonucleotide ( x i ) SEQUENCE DESCRIPTION: SEQ ID NO:18:

GGTGCAGCCT GCAGAAC 17

( 2 ) INFORMATION FOR SEQ ID NO:19:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:19:

GGATCCAGCA GGTAGTGCG 19

( 2 ) INFORMATION FOR SEQ ID NO:20:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:20:

GCAGTCAGGC CTGAGGG 17

( 2 ) INFORMATION FOR SEQ ID NO:21:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:21:

CACTGTGACA TCGGCCCAAA AG 22

( 2 ) INFORMATION FOR SEQ ID NO:22:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:22:

CCTGTCCTCA GAACCGGG 18

( 2 ) INFORMATION FOR SEQ ID NO:23:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:23:

CCAGCCAGCA GAGCTTGG     18

( 2 ) INFORMATION FOR SEQ ID NO:24:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:24:

CTGAACATGA GCTCCTTGG     19

( 2 ) INFORMATION FOR SEQ ID NO:25:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:25:

CCGGTCCACA AAGCTGGA     18

( 2 ) INFORMATION FOR SEQ ID NO:26:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:26:

CATCCGCTCA CCAGGCCTG     19

( 2 ) INFORMATION FOR SEQ ID NO:27:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:27:

AGATCTCTGC TTCTGATGGC TC     22

( 2 ) INFORMATION FOR SEQ ID NO:28:

( i ) SEQUENCE CHARACTERISTICS:
     ( A ) LENGTH: 21 base pairs
     ( B ) TYPE: nucleic acid
     ( C ) STRANDEDNESS: single
     ( D ) TOPOLOGY: linear ( i i ) MOLECULE TYPE: Other nucleic acid;
     ( A ) DESCRIPTION: Synthetic DNA oligonucleotide ( x i ) SEQUENCE DESCRIPTION: SEQ ID NO:28:

CCCTGGAGCT TGGTGACTCT G                           21

( 2 ) INFORMATION FOR SEQ ID NO:29:

( i ) SEQUENCE CHARACTERISTICS:
          ( A ) LENGTH: 19 base pairs
          ( B ) TYPE: nucleic acid
          ( C ) STRANDEDNESS: single
          ( D ) TOPOLOGY: linear ( i i ) MOLECULE TYPE: Other nucleic acid;
          ( A ) DESCRIPTION: Synthetic DNA oligonucleotide ( x i ) SEQUENCE DESCRIPTION: SEQ ID NO:29:

CCTCCTCAGT GACTCTGGC                              19

( 2 ) INFORMATION FOR SEQ ID NO:30:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( i i ) MOLECULE TYPE: Other nucleic acid;
          ( A ) DESCRIPTION: Synthetic DNA oligonucleotide ( x i ) SEQUENCE DESCRIPTION: SEQ ID NO:30:

CCGGTCCACA AAGCTGG                                17

( 2 ) INFORMATION FOR SEQ ID NO:31:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: Other nucleic acid;
          ( A ) DESCRIPTION: Synthetic DNA oligonucleotide ( x i ) SEQUENCE DESCRIPTION: SEQ ID NO:31:

CAGTTCCCTG ACTTGCACTC                             20

( 2 ) INFORMATION FOR SEQ ID NO:32:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: Other nucleic acid;
          ( A ) DESCRIPTION: Synthetic DNA oligonucleotide ( x i ) SEQUENCE DESCRIPTION: SEQ ID NO:32:

GAGAGAAGAA GGAGCGCTTC                             20

( 2 ) INFORMATION FOR SEQ ID NO:33:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Other nucleic acid;
 ( A ) DESCRIPTION: Synthetic DNA oligonucleotide ( x i ) SEQUENCE DESCRIPTION: SEQ ID NO:33:

GCAGCATATA TCTCTGCAGC 20

( 2 ) INFORMATION FOR SEQ ID NO:34:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Other nucleic acid;
 ( A ) DESCRIPTION: Synthetic DNA oligonucleotide ( x i ) SEQUENCE DESCRIPTION: SEQ ID NO:34:

CTCGGCCCTT TATCTTTGCG 20

( 2 ) INFORMATION FOR SEQ ID NO:35:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Other nucleic acid;
 ( A ) DESCRIPTION: Synthetic DNA oligonucleotide ( x i ) SEQUENCE DESCRIPTION: SEQ ID NO:35:

CCCTAACTAT AGCTCTGAGC 20

( 2 ) INFORMATION FOR SEQ ID NO:36:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i i ) MOLECULE TYPE: Other nucleic acid;
 ( A ) DESCRIPTION: Synthetic DNA oligonucleotide ( x i ) SEQUENCE DESCRIPTION: SEQ ID NO:36:

GAACCCAGGG ACTCAGCTG 19

( 2 ) INFORMATION FOR SEQ ID NO:37:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Other nucleic acid;
 ( A ) DESCRIPTION: Synthetic DNA oligonucleotide ( x i ) SEQUENCE DESCRIPTION: SEQ ID NO:37:

GGAGCTTGGT GACTCTGCTG 20

( 2 ) INFORMATION FOR SEQ ID NO:38:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: Other nucleic acid;
  ( A ) DESCRIPTION: Synthetic DNA oligonucleotide ( x i ) SEQUENCE DESCRIPTION: SEQ ID NO:38:

GCCCAATGCT CCAAAAACTC ATCC　　　　　　　　　　　　　　　　　　　　　24

( 2 ) INFORMATION FOR SEQ ID NO:39:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:39:

CAGGCCCTCA CATACCTCTC A　　　　　　　　　　　　　　　　　　　　　　21

( 2 ) INFORMATION FOR SEQ ID NO:40:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:40:

CAAAGACAGA GGATTTCCTC C　　　　　　　　　　　　　　　　　　　　　　21

( 2 ) INFORMATION FOR SEQ ID NO:41:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:41:

GTCGGCTGCT CCCTCCC　　　　　　　　　　　　　　　　　　　　　　　　17

( 2 ) INFORMATION FOR SEQ ID NO:42:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:42:

GTCTCTCGAC AGGCACAGGC　　　　　　　　　　　　　　　　　　　　　　　20

( 2 ) INFORMATION FOR SEQ ID NO:43:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:43:

GAACTGGAGG ATTCTGGAGT T        21

( 2 ) INFORMATION FOR SEQ ID NO:44:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:44:

GTGCGAGGAG ATTCGGCAGC        20

( 2 ) INFORMATION FOR SEQ ID NO:45:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:45:

CCAAAAGAAC CCGACAGCTT TC        22

( 2 ) INFORMATION FOR SEQ ID NO:46:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:46:

GCCCCAAGAA CGCACCCTGC        20

( 2 ) INFORMATION FOR SEQ ID NO:47:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:47:

GGCTCAAAGG AGTAGACTCC        20

( 2 ) INFORMATION FOR SEQ ID NO:48:

-continued ( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:48:

CAGTTCAGTG ACTATCATTC TG          22

( 2 ) INFORMATION FOR SEQ ID NO:49:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:49:

GTTGAAAGGC CTGATGGATC          20

( 2 ) INFORMATION FOR SEQ ID NO:50:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:50:

GGGGACGCAG CCATGTACC          19

( 2 ) INFORMATION FOR SEQ ID NO:51:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:51:

GGGACGCAGC CATGTACCTG          20

MONITORING AN IMMUNE RESPONSE BY ANALYSIS OF AMPLIFIED IMMUNOGLOBULIN OR T-CELL-RECEPTOR NUCLEIC ACID

RELATED APPLICATION

This application is a continuation-in-part of application Ser. No. 868,569, filed Apr. 15, 1992, abandoned.

The invention of this application was made in work funded by grants from the United States National Institutes of Health. The United States Government has certain rights in the invention.

BACKGROUND OF THE INVENTION

The present invention relates to a method, referred to here as "spectratyping," for monitoring an immune response by analyzing, and optionally comparing over time, the size distribution of amplified DNA encoding the third hypervariable region (complementary determining region, CDR3) of immunoglobulin (Ig) and T-cell receptor (TcR) molecules.

A hallmark of the immune system is its ability to recognize the extensive collection of antigens to which an organism is exposed during its lifetime. The B- and T-cell repertoires are predictive, in the sense that appropriate receptors exist prior to encountering antigen. The basis for this diverse repertoire resides in the organization of their genes. The variable regions of antibodies and TcRs are encoded by multiple gene segments that rearrange during B- and T-cell development. It is this rearrangement process that generates most of the antigen receptor diversity. The repertoires are subsequently modified according to the constraints of MHC restriction (for TcR) and tolerance to self-antigens.

The antigen binding domains of immunoglobulins (Igs) are generated during B-cell ontogeny by a process of somatic recombination between different gene segments. A very similar process occurs during T-cell development in the thymus. There are three separate loci encoding Ig chains, namely the heavy chain locus (IgH) and those for the κ and λ light chains. These loci undergo recombination at two separate stages during B-cell development, as evidenced by changes in the DNA-restriction enzyme-generated fragments of the Ig genes in mature B-cells. The first stage involves the recombination of V, D, and J segments to form the gene encoding the $V_H$ and $V_L$ domains. This takes place during differentiation of lymphoid stem cells into virgin B-cells. The second type of gene recombination may occur in the $C_H$ (constant) genes of differentiated B-cells, and is involved in irreversible class switching by the B-cell. The heavy chain constant region genes lie 3' to the recombined V-D-J gene.

The heavy chain V (variable) domain gene is assembled from a V gene encoding approximately the first 94 residues, which combines with a D (diversity) gene segment and a J (joining) gene segment. The region of the V-D-J junction forms the third hypervariable region of the V domain, while the first and second hypervariable regions are encoded within the V gene. There are more than 200 V genes in the IgH locus, with 10 D genes and 4 J genes. Since any of the V genes can recombine with any D gene and any J gene, the number of possible combinations of V-D-J is enormous. Light chain genes also undergo recombination, but these loci only contain V and J gene segments, so the third hypervariable region of the light chain is formed at a V-J junction. Recombination of either heavy or light chain genes leads to the loss of the intervening stretches of DNA, containing both introns and exons.

Recombination takes place in a defined order, with the heavy chains affected first. The process continues until functional V genes for both heavy and light chains have been generated, but the process is terminated once functional polypeptides have been synthesized. As a result, individual B cells only use one heavy chain gene and one light chain gene at random (an example of allelic exclusion).

The mechanism of recombination of Ig genes occurs efficiently only in B-cells, and appears to be directed by specific recombination sequences flanking the V, D and J exons. These sequences consist of sets of bases which can form loops by associating with sequences adjoining the next type of gene segment. These sequences are composed of a conserved heptamer, 12 or 23 unpaired bases followed by a nonamer. These are arranged in such a way that flanking sequences containing 12 unpaired bases will only recombine with one containing 23 unpaired bases. The converse is also true. These flanking sequences ensure that a light chain V segment can only recombine with a J gene, and a heavy chain V segment can only recombine with a D segment.

The recombination mechanism is not perfectly accurate and the exact point of recombination varies between cells with identical combination of V and J genes. Accordingly, the base sequences at the junction of V and J in these cells will differ slightly. Heavy chain genes also recombine with slight inaccuracies in the V-D-J junction, but in addition, extra bases may be inserted into the recombined gene on either side of the D segment. This is seen in heavy chains which contain amino acids in the D-J junction which cannot be explained by any of the possible D-J combinations in that species. The addition of extra bases in this way means that some of the bases (known as N-regions) have no origin in the germline, although the addition does not seem to be entirely at random.

Many aspects of the TcR loci are reminiscent of the Ig genes. The loci contain V, D, J and C gene segments, and somatic rearrangement must occur to generate a functional TcR gene. The rearrangement process generates most of the diverse range of receptors required to mount an effective immune response.

T-cells produce two different TcRs, the αβTcR and the γδTcR. The αβTcR predominates and will serve as the paradigm for the following discussion of TcR diversity. Both the α and β chain consist of two external Ig-like domains anchored into the plasma membrane by a transmembrane peptide and a short cytoplasmic tail.

The murine and human TcR α loci both consist of a single $C_\alpha$ gene segment separated from the $V_\alpha$ region by an extended cluster of $J_\alpha$ gene segments. No murine or human $D_\alpha$ segments have been identified. Like the $V_\beta$ genes, $V_\alpha$ segments can be divided into families of cross-hybridizing genes of between one and seven members, although the average $V_\alpha$ family size is larger. In comparison to other TcR loci, $J_\alpha$ genes are more numerous, containing at least 50 segments covering a region of around 70 kB in mice and 85 kB in humans. The $C_\alpha$ segment lies about 5 kB 3' to the most proximal $J_\alpha$ segment and encodes a shorter Ig domain than other TcR or Ig constant regions.

There are two clusters of TcR β J segments, each linked with one D gene and one C gene. The first cluster consists of Dβ1, Jβ1.1 to Jβ1.7 and Cβ1. The second cluster consists of Dβ2, Jβ2.1 to Jβ2.7 and Cβ2. The J segments and C genes in each cluster have similar nucleotide sequences.

The similarity of the genetic organizations of the B- and T-cell receptors suggests that the same rearrangement mechanisms might exist in each case. There is strong evidence that both TcR and Ig gene rearrangements share the same enzymatic machinery. The most common mechanism of gene rearrangement in T-cells involves deletion of the intervening DNA segments. It is likely that joining occurs by a two-step non-reciprocal recombination in which the first event is a precise double-stranded break between the elements to be joined and their flanking sequences. In a second step, the coding elements are joined in an imprecise event in which bases are often lost from one or both coding partners or added between the coding segments.

The ability of V, D, and J gene segments to combine together randomly introduces a large element of combinatorial diversity into the Ig and TcR repertoires. The precise point at which V, D, and J segments join can vary, giving rise to local amino acid diversity at the junction. The exact nucleotide position of joining can differ by as much as 10 residues resulting in deletion of nucleotides from the ends of the V, D, and J gene segments, thereby producing codon changes at the junctions of these segments. During the rearrangement process additional nucleotides not encoded by either gene segment can be added at the junction between the joined gene segments. (The variability created by this process is called "N-region diversity.")

Junctional diversity of TcRs greatly exceeds that of Igs. N-region diversity has been observed in all four TcR polypeptides but only in Ig heavy chains. This is one of the most significant components of the increased junctional diversity in TcRs. The variability in D region usage also increases the available diversity of TcRs. The extensive junctional flexibility of TcR V, D and J joining compensates in part for the lack of somatic mutation, and the smaller number of germline gene segments. However, this form of diversity concentrates variability within the CDR3-equivalent region, which comprises the D and/or J regions and the last few amino acids of the V region.

Because the product of each rearrangement is unique, each CDR3 region is a molecular fingerprint of the lymphocyte which generated it. Thus, an immune response can be correlated with the increase of a particular TcR or Ig. In order to observe an increase in a particular TcR or Ig, its unique CDR3 can be identified by its DNA sequence as reported by Geiger et al., *J. Immunol.* 147(7): 2082–87 (1991). But the process involves time-consuming subcloning and sequencing. A need exists, therefore, for an assay system which can be utilized to identify changes in the population of a particular TcR or Ig in order to monitor immune and, most importantly, autoimmune responses.

SUMMARY OF THE INVENTION

It is therefore an object of the present invention to provide a readily implemented approach to monitoring an immune response which involves somatic recombination between elements of at least two gene segments associated with a hypervariable region.

In accomplishing this object and others, a method for monitoring such an immune response has been provided, in accordance with one aspect of the present invention, that comprises the steps of (A) providing a sample of polynucleotide (genomic DNA or mRNA, preferably the latter) obtained from B- or T-cells of an individual; (B) subjecting the sample to an amplification which employs a first primer and a second primer, wherein the first primer is specific for a V gene segment and the second primer is specific for a C gene segment or a J gene segment of a TcR or Ig gene (a J gene segment if genomic DNA is to be employed), such that products of the amplification are amenable to resolution on the basis of a difference in length of 2 to 3 base pairs (if DNA) or 2 to 3 bases (if RNA) and then (C) determining the range of lengths represented among the products of the amplification. In a preferred embodiment, step (C) comprises separating the products electrophoretically on, for example, on an acrylamide sequencing gel under denaturing conditions. Alternatively, step (C) can comprise separating the products via capillary gel electrophoresis. Further, it is preferred that resolution of DNA fragments be such that lengths of fragments within the range, at least relative to one another, be discernible.

In accordance with another aspect of the present invention, a method as described above is provided wherein the first primer is specific for a CDR3 gene segment, such as a CDR3 gene segment coding for a portion of a T-cell receptor.

According to another aspect of the present invention, a method as described above is provided wherein the second primer is specific for one of the J segments.

According to yet another aspect of the present invention, a method is provided as described above, wherein step (A) comprises obtaining total RNA from graft-infiltrating or tumor-infiltrating lymphocytes and generating a cDNA sample therefrom for amplification in step (B). In accordance with a still further aspect of the present invention, a method as described is provided which comprises (i) effecting steps (A)–(C) at least a first time and a later second time and (ii) comparing at least the range of lengths determined at the first time with the range of lengths determined at the second time.

In addition, in accordance with the invention, the amounts, relative to a standard, of amplified products from an amplification in accordance with the invention, resolved according to size, are measured to determine the relative amounts of the underlying mRNAs or genomic DNAs, corresponding to the products of different lengths, in a sample of T-cells or B-cells from which the nucleic acid being analyzed is taken. These relative amounts may also be determined as a function of time by analyzing nucleic acid from T-cells or B-cells taken from an individual at different times.

Other objects, features and advantages of the present invention will become apparent from the following detailed description. It should be understood, however, that the detailed description and the specific examples are given by way of illustration only, since various changes and modifications within the spirit and scope of the invention will become apparent to those skilled in the art from this detailed description.

DETAILED DESCRIPTION OF THE INVENTION

Figure 1:
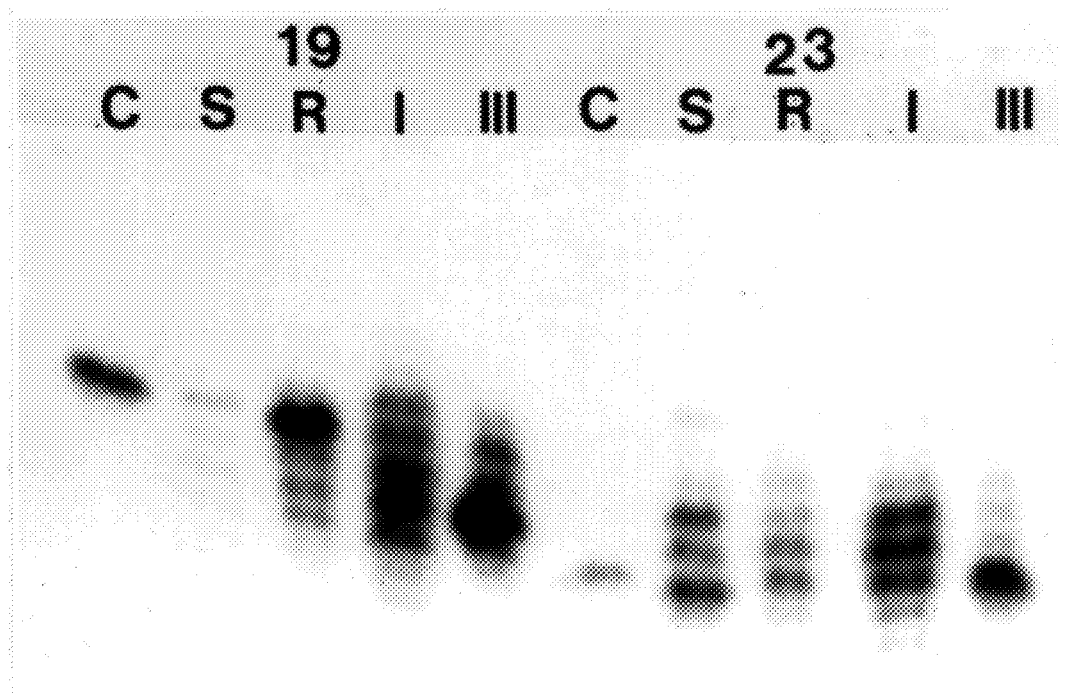
FIG. 1 show spectratype gel analyses of the CDR3 region of $V_\beta 19$-family (labelled "19") and $V_\beta 23$-family (labelled "23") T-cell receptors from T-cell cultures as described in Example 3. For each family, lane C is for a control specific for the family, lane S is the spectratype for the family in irradiated stimulator lymphocytes, lane R is the spectratype for the family in responder lymphocytes at the start (unstimulated), I is the spectratype for the family in responder lymphocytes after 1 week of stimulation, and III is the spectratype for the family in responder lymphocytes after 3 weeks of stimulation.

The present invention entails a method of monitoring an immune response by analyzing, and optionally also comparing over time, the size ranges, and typically also sizes, of amplified segments of mRNAs or genomic DNAs, which segments correspond to the CDR3 regions of Ig and TcR molecules of each of one or more classes or families.

The segments are said to "correspond to" CDR3 regions because, in some cases, Ig or TcR molecules are not expressed from mRNAs or genomic DNAs which have the segments. This is because the segments sometimes result from out-of-frame rearrangements and so have one or two too few, or one or two too many, nucleotides, thereby causing the mRNA to be out of frame for translation into an Ig or TcR molecule. Segments which do code for a CDR3 region, and, therefore, an Ig or TcR with the region, also "correspond to" the region.

Also the amounts, typically relative to some standard, of the amplification products (DNAs or RNAs, usually the former) corresponding to the different CDR3 regions for each of the classes or families will also be measured.

Thus, the methods and compositions of the present invention can be applied to the identification of the predominant TcRs in sites of autoimmune activity, such as synovial fluid in patients suffering from arthritis, cerebrospinal fluid in multiple sclerosis, and biopsied muscle in myasthenia gravis and muscular dystrophy.

These "spectratyping" methods also can be used to identify and monitor predominant TcRs in graft-infiltrating lymphocytes in patients suffering organ rejection and predominant TcRs in tumor-infiltrating lymphocytes. The method is also useful in identifying and monitoring predominant Igs in immune responses.

The spectratyping methods can also be employed to determine whether an immune response to an infectious or an autoimmune disease is "superantigen-like" or "antigen-like." It has been found that a superantigen, such as the well known bacterial superantigens, stimulate equally the production of all members (each differing in the CDR3 region) of a Vβ family of TcRβ's that respond to the superantigen, while a simple antigen, such as a specific antigenic peptide, stimulates the production of only a few members of the Vβ families of TcRβ's that respond to the antigen.

In a particularly preferred embodiment of the present invention, amplification methodologies are based on V family-specific primers. V family-specific primers are used to amplify specific groups of V family genes. Because the V family-specific primers are capable of distinguishing individual genes within the V family, the resulting amplified materials are shorter in length than materials produced using other primers and are, therefore, most suitable for resolution via spectratyping. Thus, a method within the present invention using V family-specific primers provides for a greater degree of resolution.

Preferred amplification methodologies include standard polymerase-chain-reaction (PCR) methods which are disclosed, for example, by Mullis et al., *Methods Enzymol.* 155: 335–50 (1987), and PCR modifications like "one-way" PCR and variations thereof, as disclosed by Geiger et al., "A Modified Method for "One-Way PCR": Amplification of cDNA from mRNA with Unknown 5' Ends," Methods Enzymol. (1992); and the self-sustained sequence replication method (3SR) described by Fahy et al., PCR METHODS AND APPLICATIONS (Cold Spring Harbor Laboratory Press, 1991). Quantitative PCR as disclosed by Choi et al., *Proc. Natl. Acad. Sci. USA* 86: 8941–45 (1989), is also a useful amplification method.

As described above, the present invention takes special advantage of the size heterogeneity that affects the third hypervariable region of different TcRs encoded by the same V gene. Thus, each recombined TcR associated with a V gene has N regions of varying lengths, differing amounts of the D region incorporated, and variations in the junctional positions of the V and J regions. Accordingly, a V gene family primer and a C gene primer pair will give rise to amplification products of different sizes. A finer resolution of the heterogeneity of amplified material of short length can be achieved with this method in order to quantitate TcR utilization.

V region primers are chosen as close to the carboxy terminus of the V gene as possible in a region allowing specific amplification of only the one V gene family. Some V families are represented by two primers as no unique family-specific primers can be generated. The specificity of the primers is checked by showing that amplification of cloned V genes representing all other families is negative. The following primers are exemplary of V region primers within the present invention:

|    |          |                                       | length | % C, G |
|----|----------|---------------------------------------|--------|--------|
| Vβ | 1        | CTAAACCTGAGCTCTCTGGAG (SEQ ID NO. 1)  | 21     | 52.4   |
| Vβ | 2        | GCTTCTACATCTGCAGTGC (SEQ ID NO. 2)    | 19     | 52.6   |
| Vβ | 3        | CTGGAGTCCGCCAGCACC (SEQ ID NO:3)      | 18     | 72.2   |
| Vβ | 4        | GCAACATGAGCCCTGAAG (SEQ ID NO:4)      | 18     | 55.0   |
| Vβ | 5.1, 5.2 | GATGAATGTGAGCACCTTGGAG (SEQ ID NO:5)  | 22     | 50.0   |
| Vβ | 5.3, 5.4 | GCTGAATGTGAACGCCTTGTTG (SEQ ID NO:6)  | 22     | 50.0   |

-continued

| | | | length | % C, G |
|---|---|---|---|---|
| Vβ | 6.1, 6.7, 6.8 | GATCCAGCGCACACAGC (SEQ ID NO:7) | 17 | 65.0 |
| Vβ | 6.2, 6.3, 6.4, 6.5, 6.6, 6.9, 6.10 | GATCCAGCGCACAGAGC (SEQ ID NO:8) | 17 | 65.0 |
| Vβ | 7 | CCTGAATGCCCCAACAGC (SEQ ID NO:9) | 18 | 61.0 |
| Vβ | 8 | CCAGCCCTCAGAACCCAG (SEQ ID NO:10) | 18 | 67.0 |
| Vβ | 9 | CCCTGGAGCTTGGTGACTCTGC (SEQ ID NO:11) | 22 | 63.6 |
| | | or CCCTGGAGCTTGGTGACTCTG (SEQ ID NO:28) | 21 | 61.9 |
| Vβ | 10 | CCAGTCCACGGAGTCAGG (SEQ ID NO:12) | 18 | 66.6 |
| Vβ | 11 | CCCTGGAGTCTGCCAGGC (SEQ ID NO:13) | 18 | 72.2 |
| Vβ | 12 | CTCTGGAGTCCGCTACCAG (SEQ ID NO:14) | 19 | 63.1 |
| Vβ | 13.1, 13.2 | GCTCAGGCTGCTGTCGGCTGC (SEQ ID NO:15) | 21 | 71.4 |
| Vβ | 14 | GTCTCTCGAAAAGAGAAGAGG (SEQ ID NO:16) | 21 | 47.6 |
| Vβ | 15 | CCCTAGAGTCTGCCATCC (SEQ ID NO:17) | 18 | 61 |
| Vβ | 16 | GGTGCAGCCTGCAGAAC (SEQ ID NO:18) | 17 | 64.7 |
| Vβ | 17 | GGATCCAGCAGGTAGTGCG (SEQ ID NO:19) | 19 | 63 |
| Vβ | 18 | GCAGTCAGGCCTGAGGG (SEQ ID NO:20) | 17 | 70.6 |
| | | or CCTCCTCAGTGACTCTGGC (SEQ ID NO:29) | 19 | 63.2 |
| Vβ | 19 | CACTGTGACATCGGCCCAAAAG (SEQ ID NO:21) | 22 | 54.5 |
| Vβ | 20 | CCTGTCCTCAGAACCGGG (SEQ ID NO:22) | 18 | 66.6 |
| Vβ | 21 | CCAGCCAGCAGAGCTTGG (SEQ ID NO:23) | 18 | 66.6 |
| Vβ | 22 | CTGAACATGAGCTCCTTGG (SEQ ID NO:24) | 19 | 52.6 |
| Vβ | 23 | CCGGTCCACAAAGCTGGA (SEQ ID NO:25) | 18 | 61.1 |
| | | or CCGGTCCACAAAGCTGG (SEQ ID NO:30) | 17 | 64.7 |
| Vβ | 24 | CATCCGCTCACCAGGCCTG (SEQ ID NO:26) | 19 | 68.4 |
| | | The cβ primer is set forth below: | | |
| Cβ | | AGATCTCTGCTTCTGATGGCTC (SEQ ID NO:27) | 22 | 50 |

In another preferred embodiment, V locus-specific primers can be employed. V locus-specific primers, like other locus-specific primers, hybridize with the most homologous region of the V gene which, in this case, is located furthest from the N region. Because of the distance from the N region, the resulting amplified material is longer in length than the amplified material produced using V family-specific primers. While a lesser degree of resolution is obtained using V locus-specific primers, the resulting spectratype analysis is particularly useful for the purposes of monitoring the expansion and/or contraction of particular TcR or Ig populations. Use of this embodiment, however, is not always possible because some of the loci within a gene family differ only at the amino terminus, a region too remote from the CDR3 region. Primers generated in the amino terminus portion of the V gene give rise to very long amplification products whose variable lengths may not be easily resolved.

C region primers are chosen close to the amino terminus. For TcR β chain constant regions, primers are chosen that will ensure the inclusion of an amino terminal region of the C gene in the amplified product that can distinguish Cβ1 and Cβ2, thus allowing for the identification of the constant gene by either hybridization or by sequence analysis.

Figure 4:
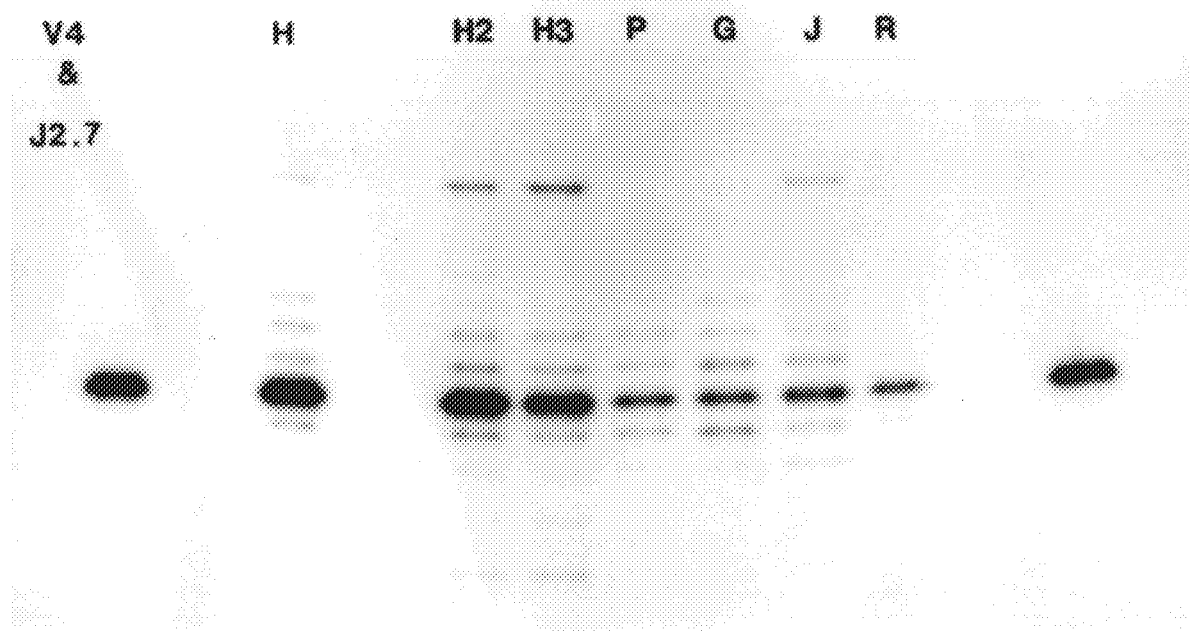
FIG. 4 shows the spectratype analysis of PBMC using two TcR Vβ primers in conjunction with a Jβ2.7 primer. The intense band seen in lanes 2, 3, and 4 corresponds to an expanded TcR clonotype (clone 4.1) which incorporated the Vβ4 and Jβ2.7 segments.

An additional level of resolution is obtained by using J region-specific primers in lieu of C region primers. This method provides for the further subdivision of every V gene family on the basis of the J region incorporated in a particular recombination. The CDR3 size heterogeneity analyzed in this manner is restricted to the particular V-J pair subjected to amplification. See FIG. 4.

As an alternative to mRNA from TcR-producing T cells or Ig-producing B cells, genomic DNA from T cells or B cells can be used as the starting material for the spectratyping method. Spectratyping starting with genomic DNA requires the use of J-specific (joining region specific) primers, due to the length of introns (on the order of 1000 bp) in genomic DNA between the joining and constant regions of a TcR or Ig gene. Amplified DNA of such length (greater than 1 kb) could not be resolved to distinguish fragments differing in length by 3 or fewer base pairs, as required for spectratyping.

Genomic DNA to be used for spectratyping can be obtained from cells or tissues by any of many published techniques. However, it is most efficient to use a method which provides both DNA and RNA from the same sample. The guanidinium/CsCl method for RNA preparation, described below, can be used. In this method, RNA pellets during centrifugation through CsCl while the DNA remains suspended in the CsCl layer. DNA can be recovered from the CsCl by either (1) removing the CsCl layer into a fresh centrifuge tube, diluting the volume of CsCl layer with an equal volume of distilled water, and centrifuging the resulting, diluted CsCl solution under the same conditions as described for preparation of RNA, whereupon the DNA is pelleted or (2) removing the CsCl layer, diluting the layer with 3 volumes of distilled water, adding ethanol in two times the volume of the resulting CsCl/DNA solution, and then pelleting the DNA by centrifugation. After either procedure, the DNA is available for amplification by PCR using desired primers.

Note that a complete spectratype for TcRβ based on genomic DNA would require 338 amplifications (26 Vβ primers×13 J primers).

A modification of spectratyping starting with genomic DNA utilizes a method wherein cells, some of which are T cells or B cells, are directly added to the First-Strand Buffer, described below, and brought to 97° C. for 5 minutes in a thermal cycler. This step lyses the cells and releases DNA, which is then available for amplification. The temperature is reduced to 50° C., the Taq enzyme, primers and dNTPs are added, and amplification is carried out. Generally 35 cycles are performed.

Because, using genomic DNA, any primer pair represents 1/200–1/400 possible V-J combinations, at least 400–500 T cells are needed to have a chance that any pair will generate at least one band. Many more cells are needed to generate full spectratypes. It appears that spectratypes using genomic DNA become fully complex when about 100,000 T cells are employed.

With reference to analysis of TcRβ's, because of the need use J-region primers when genomic DNA is employed for spectratyping, and the resultant need to carry out 338 amplifications for full spectratyping, a preferred procedure, when possible, is to first carry out spectratyping starting with mRNA, to determine which Vβ families are significant for a particular situation, and then use genomic-DNA based spectratyping for further analysis, using only the Vβ-family primers that correspond to the Vβ families that were found to be significant.

When the CDR3 region of polynucleotide (mRNA or genomic DNA) corresponding to a TcR or Ig from a sample of cells is amplified by, for example, PCR, the range of sizes (lengths) of the DNA fragments, which are the products of the amplification, are visualized by means of size-separation techniques, such as acrylamide gel electrophoresis or capillary gel electrophoresis, which resolve such fragments having lengths in the range of 100-to-300 base pairs (bp). Such resolution techniques will produce a series of bands with a spacing that corresponds to a 1–3 bp difference in size of separated fragments and the spacing of which can be visualized by any of numerous techniques. Not only the relative location of these separated bands on the separation medium (e.g., gel) but also the intensities of the bands provide useful information. The relative locations reveal the range of sizes, relative and absolute sizes, and the number of different mRNAs (or genomic DNAs) corresponding to the TcR's (or Ig's) for which the amplification was carried out (e.g., TcRβ's of a particular Vβ family). The ratio of the intensities of any two of the bands resulting from an amplification corresponds to the ratio of the numbers of mRNA (or genomic DNA) molecules, which are in the collection of T-cells (or B-cells), which are the source of nucleic acid being analyzed, and which have a segment that corresponds to the CDR3 region of a TcR (or Ig) and have a size corresponding to the location of the band on the size-separation medium (e.g., gel). The intensity of a band can be measured by any standard technique, such as measurement of fluorescence from a fluorescent label incorporated into a portion of one of the primers (e.g., the common Cβ primer in the case of analyzing Vβ families of TcR's), autoradiography made possible by the presence of $^{32}$P in a portion of such a primer, or measuring phosphorescence resulting from β-emission from a $^{32}$P-label on such a primer using, for example, a phosphorescence-based β-counter from Ambis, Inc. (San Diego, Calif., USA).

In addition, the bands represent not just the number of distinct TcR of a particular size but also the expansion of the population of any particular TcR and may be analyzed to yield information on the relative amount of the TcR of a particular size relative to all TcR's of the same Vβ family. An intense band therefore may signify that many different TcR of a particular size are present in a sample, or that a particular TcR population has expanded and now accounts for a majority of the TcR population of that size class present in a sample. Changes in intensity signify expansion or contraction of particular T-cell populations.

As an immune response commences, matures and then phases out (i.e., "progresses"), populations of TcRs of an individual will change. Thus, a spectratype analysis at different times in accordance with the present invention provides a quick and reliable means of monitoring the individual's immune status and the progress of the individual's immune response. Preferred methods of electrophoretic resolution of this material include polyacrylamide gel electrophoresis and high-performance capillary gel electrophoresis as disclosed by Cohen et al., *Proc. Natl. Acad. Sci. USA* 448: 41–53 (1988).

In addition to providing a means of determining quantitatively the amount of various V gene family TcRs in a sample, spectratype bands can be eluted from a gel, amplified further as needed, subcloned, and used to determine the nucleic acid sequence of particular clonotypes. In this way the TcR complexity associated with each CDR3 size class can be determined. Once the sequences of predominant clonotypes within a size class have been determined, clonotype-specific probes can be generated. These probes can be used to quantitate individual clonotypes found in spectratypes during adoptive transfers, for example, by electroblotting a spectratype onto a nylon membrane and then hybridizing the bands with J region or clonotype-specific probes.

Spectratyping methods within the present invention can be used to monitor relapse after onset of autoimmune disease. Identical spectratypes in both the primary episodes and subsequent incidence of relapse indicate that the same population of T-cells is responsible for all episodes. Such a finding indicates that a partial suppression of the autoimmune response occurs followed by a recovery of the same T-cell population. On the other hand, the finding that different spectratypes were present in each autoimmune episode would indicate that the suppression of one population of T-cells allows another population to become the predominant effector population.

A complete spectratype of the TcRβ repertoire of an individual requires 26 separate amplifications if a common C-region primer is used, one for each of 26 Vβ family primers. If the full repertoire of J-region primers is used, 338 (i.e., 26×13) amplifications would be required. These numbers of amplifications are for a spectratype done at only a single time point. It clearly would be advantageous to reduce the number of amplification reaction procedures, associated tubes or wells, and separation procedures (e.g., gel electrophoreses) that would be required to carry out and analyze the results of these large number of amplifications.

Figure 5:
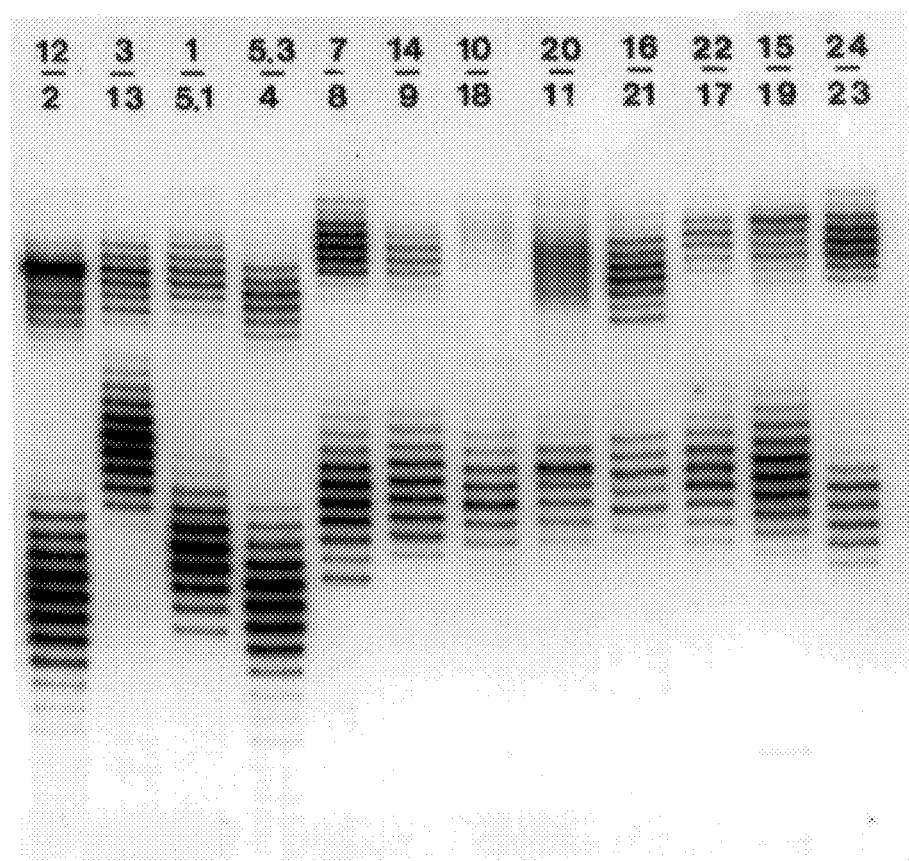
FIG. 5 shows a set of spectratyping gels on which the products of amplification of mRNA from a sample of T cells using a single TcRβ constant-region primer (the Cβ primer of sequence SEQ ID NO:27) and pairs of Vβ-family primers in each amplification. The Vβ families in each pair are indicated by the numbers above each lane. The number on top in each lane is for the Vβ family of the amplification products on top in the lane as shown in the Figure.

As illustrated in FIG. 5, it has now been found to be possible to combine two Vβ primers (other than those for the Vβ6 family) in a single spectratyping amplification procedure and obtain two sets of amplification products, one from the amplification with one of the Vβ primers and the other from amplification with the other of the Vβ primers, that can be separated sufficiently from one another to avoid overlap and that, within each set, can be resolved by the 2–3 base pairs required for spectratyping, using the separation techniques that are used when the products of amplification using a single Vβ primer are analyzed. This discovery, that two Vβ primers can be combined to carryout spectratypes simultaneously for two Vβ families, is also part of the present invention.

In this regard, it has been found that the primers indicated in the following Table are particularly useful. In general, any primer indicated as being "long" (meaning that the fragments generated with the primer and the Cβ primer (SEQ ID NO:27) are longer than those generated with any of the primers designated as "short") can be used with any primer indicated as being "short." The table of primers lists those that were used to generate FIG. 5, which provides guidance on the separation between fragments generated with "long" and "short" (or "shortish") primers.

Each of the primers listed in the Table can also be used by itself (along with a constant- or joining-region primer) in spectratyping.

Note also that although amplifications with the primer for Vβ 6.1 (SEQ ID NO:7) must be run separately from those with the primer for Vβ 6.2 (SEQ ID NO:8), the products of the two amplifications can be resolved in the same gel lane, if the products of the 6.1 amplification are added to the lane about 30 minutes after the products of the 6.2 amplification.

TE Solution
   10 nM Tris, pH 7.0
   1 mM EDTA
5.7 M CsCl
   96 g CsCl
   add TE solution to a final volume of 100 ml
40% CsCl
   40 g CsCl
   add TE solution to a final volume of 100 ml

EXAMPLE 1

Amplification for Spectratyping
  A. RNA Preparation/Guanidinium Method

Day 1

Discontinuous cesium gradients were prepared by adding 1.5 ml of 5.7M CsCl to polyallomer centrifuge tubes which

TABLE

| | | | | |
|---|---|---|---|---|
| VB1 | Long | CAGTTCCCTGACTTGCACTC (SEQ ID NO:31) | 20 mer | 11 G/C |
| VB2 | Short | GCTTCTACATCTGCAGTGC (SEQ ID NO:32) | 19 mer | 10 G/C |
| VB3 | Long | GAGAGAAGAAGGAGCGCTTC (SEQ ID NO:33) | 20 mer | 11 G/C |
| VB4 | Short | GCAGCATATATCTCTGCAGC (SEQ ID NO:34) | 20 mer | 11 G/C |
| VB5.1 | Short | CTCGGCCCTTTATCTTTGCG (SEQ ID NO:35) | 20 mer | 11 G/C |
| VB5.3 | Long | CCCTAACTATAGCTCTGAGC (SEQ ID NO:36) | 20 mer | 10 G/C |
| VB6.1 | Medium | GATCCAGCGCACACAGC (SEQ ID NO:37) | 17 mer | 11 G/C |
| VB6.2 | Medium | GATCCAGCGCACAGAGC (SEQ ID NO:38) | 17 mer | 11 G/C |
| VB7 | Long | CCTGAATGCCCCAACAGC (SEQ ID NO:39) | 18 mer | 11 G/C |
| VB8 | Short | GAACCCAGGGACTCAGCTG (SEQ ID NO:40) | 19 mer | 12 G/C |
| VB9 | Short | GGAGCTTGGTGACTCTGCTG (SEQ ID NO:41) | 20 mer | 12 G/C |
| VB10 | Long | GCCCAATGCTCCAAAAACTCATCC (SEQ ID NO:42) | 24 mer | 12 G/C |
| VB11 | Short | CAGGCCCTCACATACCTCTCA (SEQ ID NO:43) | 21 mer | 12 G/C |
| VB12 | Long | CAAAGACAGAGGATTTCCTCC (SEQ ID NO:44) | 21 mer | 10 G/C |
| VB13 | Shortish | GTCGGCTGCTCCCTCCC (SEQ ID NO:45) | 17 mer | 13 G/C |
| VB14 | Long | GTCTCTCGAAAAGAGAAGAGG (SEQ ID NO:46) | 21 mer | 10 G/C |
| VB15 | Long | GTCTCTCGACAGGCACAGGC (SEQ ID NO:47) | 20 mer | 13 G/C |
| VB16 | Short | GAACTGGAGGATTCTGGAGTT (SEQ ID NO:48) | 21 mer | 10 G/C |
| VB17 | Short | GTGCGAGGAGATTCGGCAGC (SEQ ID NO:49) | 20 mer | 13 G/C |
| VB18 | Short | CCTCCTCAGTGACTCTGGC (SEQ ID NO:50) | 19 mer | 12 G/C |
| VB19 | Short | CCAAAAGAACCCGACAGCTTTC (SEQ ID NO:51) | 22 mer | 11 G/C |
| VB20 | Long | GCCCCAAGAACGCACCCTGC | 20 mer | 14 G/C |
| VB21 | Long | GGCTCAAAGGAGTAGACTCC | 20 mer | 11 G/C |
| VB22 | Long | CAGTTCAGTGACTATCATTCTG | 22 mer | 9 G/C |
| VB23 | Long | GTTGAAAGGCCTGATGGATC | 20 mer | 10 G/C |
| VB24 | Short | GGGGACGCAGCCATGTACC | 19 mer | 13 G/C |
| | | or GGGACGCAGCCATGTACCTG | 20 mer | 13 G/C |

In light of the preceding description, one skilled in the immunological arts can use the present invention to its fullest extent. The following examples therefore are to be construed as illustrative only and not limiting in relation to the remainder of the disclosure. The following buffers and solutions are employed in the examples:

5×First Strand Buffer
  250 mM Tris pH 8.3
  375 mM KCl
  15 mM MgCl$_2$
  50 mM dithiothreitol Taq Supplement
  0.04% Gelatin
  50.0 mM KCl Guanidinium Isothiocyanate Buffer (GIB)
  25.0 g guanidinium isothiocyanate
  40.0 ml H$_2$O Warm in bath to facilitate dissolution
  Add:
    0.37 g trisodium citrate (MW 294.1)
    0.25 g Sarcosyl (N-lauryl sarcosine) Adjust pH to 7.0 with 1M NaOH
Add H$_2$O to final volume of 50 ml.
Filter sterilize and store in brown glass bottle (light sensitive). Discard after three weeks.

fit an Sw 60 (Beckman) rotor. The 5.7M CsCl is gently overlaid with 500 μl of 40% CsCl. The level of each gradient was marked after addition of each CsCl solution and the tube was numbered.

Under a fume hood, 79 μl of mercaptoethanol was added to 9.9 ml of GIB. The resulting solution was mixed and placed on ice. Frozen cells, i.e., PBBC, T-cell lines or tissue cells, were removed from a −70° C. freezer and the tubes containing the frozen cells were kept on powdered dry ice. 0.7 to 2.0 ml of GIB was added to the tubes containing the frozen cells. While kept on ice, a homogenizer (Tissue Mizer), first rinsed with water and then with GIB, was used to homogenize the cells for approximately 30 seconds. The homogenized cell solution was then layered over the 40% CsCl gradient of a CsCl gradient tube. If the homogenized cell solution volume was insufficient, a small aliquot of GIB was used to rinse the tube containing the frozen homogenized cells and then added to the homogenized cell solution in the tube containing CsCl gradients. Homogenized cell solutions were overlayed with enough TE to fill the tubes to the brim. The tubes were weighed and assembled in pairs of matching weights for centrifugation. The tubes were centrifuged for 18 hours at 36,000 rpm in a Sw 60 (Beckman) rotor at 20° C.

Day 2

After the tubes were removed from the centrifuge, the supernatant was collected with a pipette down to the 5.7 mM CsCl gradient level. The tubes were cut and the remaining CsCl discarded. The tubes then were placed upside down on paper towels to drain. In order to resuspend the RNA pellet, 100 μl of H$_2$O was added to each cut tube, swirled around and then transferred to a siliconized, diethyl pyrocarbonate (DEP) treated Eppendorf tube. This procedure was repeated twice in order to ensure that the entire RNA pellet was transferred to the Eppendorf tubes. 30 μl of sodium acetate was added to each tube and mixed well. Absolute ethanol (700 μl) then was added to each tube, vortexed and stored at −20° C. for a minimum of 8 hours.

B. First Strand Synthesis

The following ingredients were added to siliconized and DEP-treated 0.5 ml microcentrifuge tubes that were kept on ice:

10.0 μl total RNA (5–20 μg)
    2.5 μl 10 mM dNTP (deoxyadenosine triphosphate, deoxycytidine triphosphate, deoxyguanosine triphosphate, thymidine triphosphate) mix
    10.0 μl oligo (dT) primer
    15.0 μl sterile filtered dd H$_2$O
    10.0 μl First Strand Buffer
    2.5 μl M-MLV reverse transcriptase
    50.0 μl Final Volume The final composition of the first strand reaction was:

50 mM Tris pH 8.3
75 mM KCl
3 mM MgCl$_2$
10 mM dithiothreitol 0.5 mM dNTP
2 μM anti-RNA primer 100–400 μg/ml RNA
500 U reverse transcriptase MMLV The tubes were incubated at 42° C. for 1 hour and then placed on ice. 25 μl of Taq Supplement, 10 μl of the 1M second primer and 15 μl of sterile filtered H$_2$O was added to each tube. The resulting solutions were boiled for 2 minutes to denature the RNA. After cooling, 2.5 U of Taq Polymerase and approximately 100 μl of mineral oil was added to each tube. The tubes were vortexed briefly and then placed in a thermal cycler. 25×cycles were: 1.5 minutes at 95° C.; 1.5 minutes at 50° C.; and 1.5 minutes at 73° C.

C. PCR for Spectratype Analysis

The PCR mix (40 μl of final volume) for spectratyping contained labelled Constant region primer added as a tracer to excess unlabelled Constant region primer. The reaction was cycled 30 times which has been found to provide adequate material for a spectratype for human blood PBMC or mouse spleen samples and, at the same time, maintain a correspondence between the intensities of the amplified bands to the amount of starting material. RNA starting material was prepared by the guanidinium/CsCl method.

The amount of starting cDNA was defined as RNA equivalents. In other words, 1 μg of RNA converted into total cDNA in a reverse transcription assay with a 50 μl volume was considered to be equivalent to 1 μg of cDNA (assumes 100% conversion). Thus 1 μl of the above reaction was assumed to contain 20 ng cDNA. It was determined that 20 to 60 ng of cDNA were sufficient to obtain spectratypes from human blood PBMC or mouse spleen cells. Additional starting material must be employed or the PCR run for additional cycles when analyzing a tissue where T-cells are normally found only in disease states, for example, synovium, nerve tissue and tumors.

A 20 ng PCR requires the following ingredients:

X μl reverse transcription reaction to give 20 ng cDNA
10 μl Taq supplement (see RNA PCR method of Example 2)
4 μl First strand buffer
2 μl Constant primer, unlabelled
2 μl Variable gene family primer
1 μl labelled Constant region primer
1 μl Taq supplement
Y μl H$_2$O to final volume of 40 μl An oligonucleotide primer labelled with $^{32}$P using the kinase reaction did not migrate in the same position on a gel as an unlabelled primer. For this reason, when recovering bands from the gel for further analysis, the cold Constant region primer also underwent a kinase reaction but with unlabelled ATP as the phosphate source. The bulk of the DNA migrated at the position of the radioactive tracer. An autoradiograph was used to determine where to cut the gel to recover the DNA.

Five microliters of the reaction mixture were added to sequence gel loading buffer and loaded on a 5% polyacrylamide/urea sequencing gel. The gel was run very hot, i.e., 55° C., in order to assure maintenance of the denatured state of the PCR products. An autoradiogram of the gel was employed to localize, count and quantitate the bands.

Figure 3:
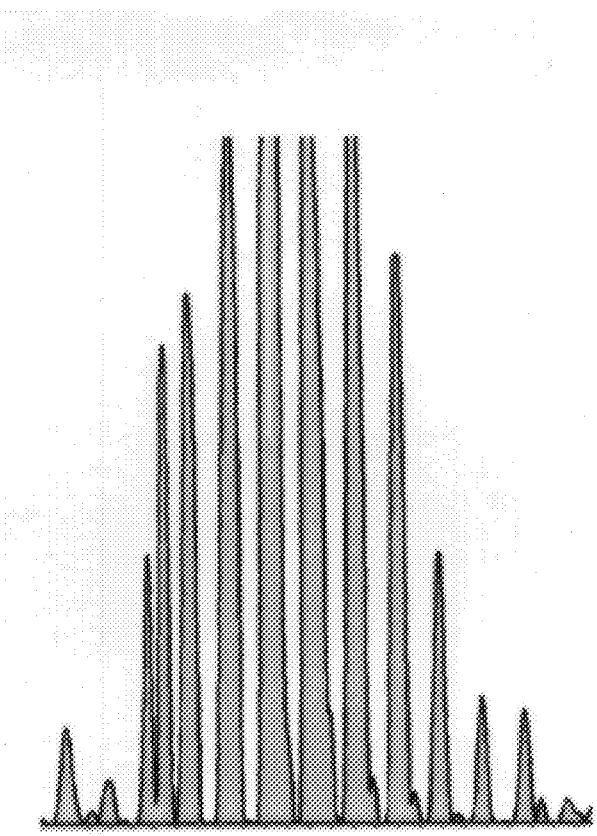
FIG. 3 shows the analysis of a Vβ4-specific amplification using FITC-labelled constant region primer employing a fluorescence-based DNA sequencer. The ordinate is relative fluorescence intensity. The abscissa is DNA segment size. The major peaks represent fragments that differ by multiples of 3 bp in size.

As an alternative to radioactive labeling and autoradiography, a fluorescent dye was attached to primer 2 (C or J region primer). The resulting spectratype was analyzed by exciting the dye at one wavelength and detecting the resulting emission at another wavelength. This was accomplished using a lamp and filtered camera or with a specialized fluorescence detecting apparatus. The results of an analysis performed with FITC labeled constant region primer in a Vβ4-specific amplification and employing an ABI 373 fluorescence-based DNA sequencer are depicted in FIG. 3. The area under the peak reflects the intensity of the DNA bands separated on a DNA sequencing gel. Using the appropriate software, the band was quantified and compared with known standards.

EXAMPLE 2

Kinase Labeling of Oligonucleotide Probes

Labeling of oligonucleotide probes was accomplished by preparing the following solution:

2 μl DNA
1 μl 10X kinase buffer (according to manufacturer's instructions)
6.5 μl gamma AT$^{32}$P
0.5 μl enzyme (kinase)

The resulting solution was first incubated at 37° C. for 30 minutes and then at 65° C. for 10 minutes to stop the enzyme. 26.35 μl of 0.1 M NaCl containing 0.5% SDS and 3.65 μl of herring DNA were then added to each tube.

Non-incorporated AT$^{32}$P was separated from labelled oligonucleotide probe using small columns comprised of siliconized pasteur pipettes packed with siliconized glass wool and superfine G50 which were eluted with TE. Alternatively, non-incorporated AT$^{32}$P was left in the reaction since its small size does not interfere with the spectratype analysis.

EXAMPLE 3

Spectratype Analysis of In Vitro Stimulated T-Cell Cultures

Analysis of in vitro cultures by spectratyping was undertaken using an alloreactive human MLC culture. PBMC were cultured with irradiated allogeneic stimulator cells for three cycles of priming. Spectratypes of different TcR $V_\beta$ families were performed. Shifts in spectratypes were easily visualized. Some $V_\beta$ families became monoclonal, some became more complex, while others disappeared entirely. The results of the spectratype analysis are depicted in FIG. 1. Shifts were observed for both the $V_\beta 19$ and $V_\beta 23$ families over a period of three weeks.

EXAMPLE 4

Spectratyping of Spleen, Brain and Spinal Cord Infiltrating T-Cells

Total RNA was prepared from mouse SJL spleen, brain and spinal cord, converted to cDNA and PCR amplified with $V_\beta 4$ and $V_\beta 17$ specific primers according to the methodology of Example 1. The C region primer was labelled with $^{32}P$ using ATP and kinase according to the methodology of Example 2. Equal amounts of cDNA (200 ng RNA equivalent) was used for each sample and the PCR performed for 30 cycles for spleen cDNA and 60 cycles for brain and spinal cord cDNA. The mice were exhaustively perfused with PBS prior to harvesting the tissues. The spectratype gel was exposed overnight. The results of the spectratype analysis are depicted in FIG. 2.

Figure 2:
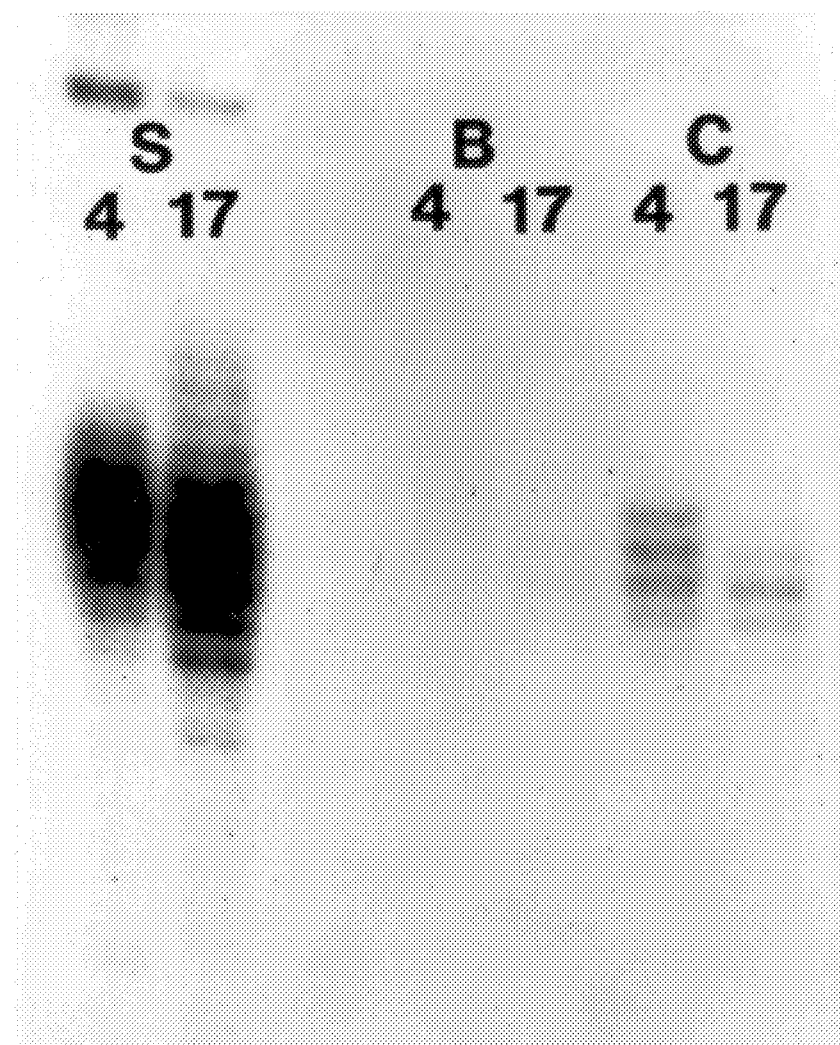
FIG. 2 shows spectratypes for the $V_\beta 4$-family (labeled "4") and $V_\beta 17$-family (labeled "17") of T lymphocytes from the spleen (labeled "S") , the brain (labeled "B") , and the spinal cord (labeled "C") of a mouse with autoimmune encephalitis. See Example 4.

FIG. 2 illustrates that the $V_\beta 17$ spectratype of the spinal cord infiltrating T-cells (Lane C) was not monoclonal as five bands are visible. A predominant band exists, however, which corresponds with one of the splenic bands (Lane S). The spleen and spinal cord spectratypes show distinctly different patterns.

EXAMPLE 5

Hybridization Analysis of TcR cDNA Recovered and Reamplified from the Bands of a Spectratype Bands labelled 2–14 in a spectratype of $V_\beta 4$-family TcR's on a gel lane were cut out and the cDNA eluted by overnight diffusion into TE.

The cDNA in 1 $\mu l$ of the solution of the cDNA eluted from each of the bands into TE was reamplified using primers identical to those used for the initial spectratype except that the $V_\beta 4$-family specific primer had a restriction site added. An aliquot which comprised approximately $\frac{1}{20}$ of the amplified material was electrophoresed through one lane of a 1% agarose gel. 15 lanes were run in parallel—one for each of the 13 reamplification procedures, one with a $\Phi X$ size marker, and one with a positive control (amplification of clone 4.1 and clone 4.3 cDNA using the same primers). Reamplification of the DNA eluted from all 13 of the spectratype bands yielded amplified material. The DNA from the gel was transferred to nylon filter and hybridized with a clone 4.1 and a clone 4.3 specific probe. The 4.1 probe hybridized with DNA from reamplification of the cDNA from band 8 of the spectratype. Band 8 was the most predominant band in the spectratype and was suspected to correspond to the most predominant clone (namely, 4.1). The 4.3 probe hybridized as expected with DNA from reamplification of the cDNA from band 6 of the spectratype. The CDR3 of TcR CDNA of clone 4.3 is 6 bp longer than that of clone 4.1 and so was expected in band 6. Cross-contamination resulting from the cutting out of the gel bands of the spectratype caused hybridization of the 4.3 probe to reamplified DNA from band 5 of the spectratype.

I claim:

1. A method for the monitoring of an immune response that involves somatic recombination between elements of at least two gene segments associated with a hypervariable region, comprising the steps of
(A) providing a sample of a polynucleotide obtained from B- or T-cells of an individual;
(B) subjecting said sample to an amplification which employs a first primer and a second primer, wherein said first primer is specific for a variable gene segment and said second primer is specific for a constant or a joining gene segment of said individual, such that products of said amplification are amenable to resolution on the basis of a difference in length between of 2 to 3 base pairs;
(C) separating said products of said amplification by a technique whereby products with lengths differing by 3 base pairs can be resolved;
(D) determining the range of lengths represented among said separated products to obtain a spectratype of the immune response of the individual; and
(E) comparing the spectratype to a previously obtained standard to determine the immune status of the individual and monitor the immune response.

2. A method according to claim 1, wherein step (C) comprises separating said products electrophoretically.

3. A method according to claim 2, wherein step (C) comprises separating said products via electrophoresis on an acrylamide sequencing gel under denaturing conditions.

4. A method according to claim 2, wherein step (C) comprises separating said products via capillary gel electrophoresis.

5. A method according to claim 1, wherein the sample of polynucleotide comprises mRNAs encoding immunoglobulins or T-cell receptors and the products of the amplification comprise segments of cDNAs reverse transcribed from such mRNAs.

6. A method according to claim 5 wherein the first primer is specific for a variable gene segment, which is outside a third hypervariable, CDR3, gene segment and said second primer is specific for a constant gene segment.

7. A method according to claim 3, wherein the sample of polynucleotide comprises mRNAs encoding immunoglobulins or T-cell receptors and the products of the amplification comprise segments of cDNAs reverse transcribed from such mRNAs.

8. A method according to claim 7 wherein the first primer is specific for a variable gene segment, which is outside a third hypervariable, CDR3, gene segment and said second primer is specific for a constant gene segment.

9. A method according to claim 4, wherein the sample of polynucleotide comprises mRNAs encoding immunoglobulins or T-cell receptors and the products of the amplification comprise segments of cDNAs reverse transcribed from such mRNAs.

10. A method according to claim 9 wherein the first primer is specific for a variable gene segment, which is outside a third hypervariable, CDR3, gene segment and said second primer is specific for a constant gene segment.

11. A method according to claim 6, wherein said third hypervariable, CDR3, gene segment codes for a portion of a T-cell receptor.

12. A method according to claim 8, wherein said third hypervariable, CDR3, gene segment codes for a portion of a T-cell receptor.

13. A method according to claim 10, wherein said third hypervariable, CDR3, gene segment codes for a portion of a T-cell receptor.

14. A method according to claim 1, wherein the second primer is specific for a joining segment.

15. A method according to claim 3, wherein the second primer is specific for a joining segment.

16. A method according to claim 4, wherein the second primer is specific for a joining segment.

17. A method according to claim 1, wherein step (A) comprises obtaining total RNA from graft infiltrating or tumor infiltrating lymphocytes and generating a cDNA sample therefrom for amplification in step (B).

18. A method according to claim 11, wherein step (A) comprises obtaining total RNA from graft infiltrating lymphocytes and generating a cDNA sample therefrom for amplification in step (B).

19. A method according to claim 12, wherein step (A) comprises obtaining total RNA from graft infiltrating lymphocytes and generating a CDNA sample therefrom for amplification in step (B).

20. A method according to claim 13, wherein step (A) comprises obtaining total RNA from graft infiltrating lymphocytes and generating a cDNA sample therefrom for amplification in step (B).

21. A method according to claim 1, wherein step (E) further comprises (i) effecting steps (A)–(D) at least a first time and a later second time and (ii) comparing the range of lengths determined at said first time with the range of lengths determined at said second time.

22. A method according to claim 11 wherein, in step (B), the first primer is selected from the group consisting of

Vβ 1 CTAAACCTGAGCTCTCTGGAG (SEQ ID NO:1),

Vβ 2 GCTTCTACATCTGCAGTGC (SEQ ID NO:2),

Vβ 3 CTGGAGTCCGCCAGCACC (SEQ ID NO:3),

Vβ 4 GCAACATGAGCCCTGAAG (SEQ ID NO:4),

Vβ 5.1 GATGAATGTGAGCACCTTGGAG (SEQ ID NO:5),

Vβ 5.2 GATGAATGTGAGCACCTTGGAG (SEQ ID NO:5),

Vβ 5.3 GCTGAATGTGAACGCCTTGTTG (SEQ ID NO:6),

Vβ 5.4 GCTGAATGTGAACGCCTTGTTG (SEQ ID NO:6),

Vβ 6.1 GATCCAGCGCACACAGC (SEQ ID NO:7),

Vβ 6.3 GATCCAGCGCACACAGC (SEQ ID NO:7),

Vβ 6.4 GATCCAGCGCACACAGC (SEQ ID NO:7),

Vβ 6.2 GATCCAGCGCACAGAGC (SEQ ID NO:8),

Vβ 6.7 GATCCAGCGCACAGAGC (SEQ ID NO:8),

Vβ 6.8 GATCCAGCGCACAGAGC (SEQ ID NO:8),

Vβ 6.5 GATCCAGCGCACAGAGC (SEQ ID NO:8),

Vβ 6.6 GATCCAGCGCACAGAGC (SEQ ID NO:8),

Vβ 6.9 GATCCAGCGCACAGAGC (SEQ ID NO:8),

Vβ 6.10 GATCCAGCGCACAGAGC (SEQ ID NO:8),

Vβ 18 GATCCAGCGCACAGAGC (SEQ ID NO:8),

Vβ 7 CCTGAATGCCCCAACAGC (SEQ ID NO:9),

Vβ 8 CCAGCCCTCAGAACCCAG (SEQ ID NO:10),

Vβ 9 CCCTGGAGCTTGGTGACTCTGC (SEQ ID NO:11),

Vβ 10 CCAGTCCACGGAGTCAGG (SEQ ID NO:12),

Vβ 11 CCCTGGAGTCTGCCAGGC (SEQ ID NO:13),

Vβ 12 CTCTGGAGTCCGCTACCAG (SEQ ID NO:14),

Vβ 13.1 GCTCAGGCTGCTGTCGGCTGC (SEQ ID NO:15),

Vβ 13.2 GCTCAGGCTGCTGTCGGCTGC (SEQ ID NO:15),

Vβ 14 GTCTCTCGAAAAGAGAAGAGG (SEQ ID NO:16),

Vβ 15 CCCTAGAGTCTGCCATCC (SEQ ID NO:17),

Vβ 16 GGTGCAGCCTGCAGAAC (SEQ ID NO:18),

Vβ 17 GGATCCAGCAGGTAGTGCG (SEQ ID NO:19),

Vβ 18 GCAGTCAGGCCTGAGGG (SEQ ID NO:20),

Vβ 19 CACTGTGACATCGGCCCAAAAG (SEQ ID NO:21),

Vβ 20 CCTGTCCTCAGAACCGGG (SEQ ID NO:22),

Vβ 21 CCAGCCAGCAGAGCTTGG (SEQ ID NO:23),

Vβ 22 CTGAACATGAGCTCCTTGG (SEQ ID NO:24),

Vβ 23 CCGGTCCACAAAGCTGGA (SEQ ID NO:25), and

Vβ 24 CATCCGCTCACCAGGCCTG (SEQ ID NO:26), and the second primer is Cβ AGATCTCTGCTTCTGATGGCTC (SEQ ID NO:27).

23. A method according to claim 12 wherein, in step (B), the first primer is selected from the group consisting of

Vβ 1 CTAAACCTGAGCTCTCTGGAG (SEQ ID NO:1),

Vβ 2 GCTTCTACATCTGCAGTGC (SEQ ID NO:2),

Vβ 3 CTGGAGTCCGCCAGCACC (SEQ ID NO:3),

Vβ 4 GCAACATGAGCCCTGAAG (SEQ ID NO:4),

Vβ 5.1 GATGAATGTGAGCACCTTGGAG (SEQ ID NO:5),
Vβ 5.2 GATGAATGTGAGCACCTTGGAG (SEQ ID NO:5),
Vβ 5.3 GCTGAATGTGAACGCCTTGTTG (SEQ ID NO:6),
Vβ 5.4 GCTGAATGTGAACGCCTTGTTG (SEQ ID NO:6),
Vβ 6.1 GATCCAGCGCACACAGC (SEQ ID NO:7),
Vβ 6.3 GATCCAGCGCACACAGC (SEQ ID NO:7),
Vβ 6.4 GATCCAGCGCACACAGC (SEQ ID NO:7),
Vβ 6.2 GATCCAGCGCACAGAGC (SEQ ID NO:8),
Vβ 6.7 GATCCAGCGCACAGAGC (SEQ ID NO:8),
Vβ 6.8 GATCCAGCGCACAGAGC (SEQ ID NO:8),
Vβ 6.5 GATCCAGCGCACAGAGC (SEQ ID NO:8),
Vβ 6.6 GATCCAGCGCACAGAGC (SEQ ID NO:8),
Vβ 6.9 GATCCAGCGCACAGAGC (SEQ ID NO:8),
Vβ 6.10 GATCCAGCGCACAGAGC (SEQ ID NO:8),
Vβ 18 GATCCAGCGCACAGAGC (SEQ ID NO:8),
Vβ 7 CCTGAATGCCCCAACAGC (SEQ ID NO:9),
Vβ 8 CCAGCCCTCAGAACCCAG (SEQ ID NO:10),
Vβ 9 CCCTGGAGCTTGGTGACTCTGC (SEQ ID NO:11),
Vβ 10 CCAGTCCACGGAGTCAGG (SEQ ID NO:12),
Vβ 11 CCCTGGAGTCTGCCAGGC (SEQ ID NO:13),
Vβ 12 CTCTGGAGTCCGCTACCAG (SEQ ID NO:14),
Vβ 13.1 GCTCAGGCTGCTGTCGGCTGC (SEQ ID NO:15),
Vβ 13.2 GCTCAGGCTGCTGTCGGCTGC (SEQ ID NO:15),
Vβ 14 GTCTCTCGAAAAGAGAAGAGG (SEQ ID NO:16),
Vβ 15 CCCTAGAGTCTGCCATCC (SEQ ID NO:17),
Vβ 16 GGTGCAGCCTGCAGAAC (SEQ ID NO:18),
Vβ 17 GGATCCAGCAGGTAGTGCG (SEQ ID NO:19),
Vβ 18 GCAGTCAGGCCTGAGGG (SEQ ID NO:20),
Vβ 19 CACTGTGACATCGGCCCAAAAG (SEQ ID NO:21),
Vβ 20 CCTGTCCTCAGAACCGGG (SEQ ID NO:22),
Vβ 21 CCAGCCAGCAGAGCTTGG (SEQ ID NO:23),
Vβ 22 CTGAACATGAGCTCCTTGG (SEQ ID NO:24),
Vβ 23 CCGGTCCACAAAGCTGGA (SEQ ID NO:25), and
Vβ 24 CATCCGCTCACCAGGCCTG (SEQ ID NO:26), and
the second primer is Cβ AGATCTCTGCTTCTGATGGCTC (SEQ ID NO:27).

24. A method according to claim 13 wherein, in step (B), the first primer is selected from the group consisting of
Vβ 1 CTAAACCTGAGCTCTCTGGAG (SEQ ID NO:1),
Vβ 2 GCTTCTACATCTGCAGTGC (SEQ ID NO:2),
Vβ 3 CTGGAGTCCGCCAGCACC (SEQ ID NO:3),
Vβ 4 GCAACATGAGCCCTGAAG (SEQ ID NO:4),
Vβ 5.1 GATGAATGTGAGCACCTTGGAG (SEQ ID NO:5),
Vβ 5.2 GATGAATGTGAGCACCTTGGAG (SEQ ID NO:5),
Vβ 5.3 GCTGAATGTGAACGCCTTGTTG (SEQ ID NO:6),
Vβ 5.4 GCTGAATGTGAACGCCTTGTTG (SEQ ID NO:6),
Vβ 6.1 GATCCAGCGCACACAGC (SEQ ID NO:7),
Vβ 6.3 GATCCAGCGCACACAGC (SEQ ID NO:7),
Vβ 6.4 GATCCAGCGCACACAGC (SEQ ID NO:7),
Vβ 6.2 GATCCAGCGCACAGAGC (SEQ ID NO:8),
Vβ 6.7 GATCCAGCGCACAGAGC (SEQ ID NO:8),
Vβ 6.8 GATCCAGCGCACAGAGC (SEQ ID NO:8),
Vβ 6.5 GATCCAGCGCACAGAGC (SEQ ID NO:8),
Vβ 6.6 GATCCAGCGCACAGAGC (SEQ ID NO:8),
Vβ 6.9 GATCCAGCGCACAGAGC (SEQ ID NO:8),
Vβ 6.10 GATCCAGCGCACAGAGC (SEQ ID NO:8),
Vβ 18 GATCCAGCGCACAGAGC (SEQ ID NO:8),
Vβ 7 CCTGAATGCCCCAACAGC (SEQ ID NO:9),
Vβ 8 CCAGCCCTCAGAACCCAG (SEQ ID NO:10),
Vβ 9 CCCTGGAGCTTGGTGACTCTGC (SEQ ID NO:11),
Vβ 10 CCAGTCCACGGAGTCAGG (SEQ ID NO:12),
Vβ 11 CCCTGGAGTCTGCCAGGC (SEQ ID NO:13),
Vβ 12 CTCTGGAGTCCGCTACCAG (SEQ ID NO:14),
Vβ 13.1 GCTCAGGCTGCTGTCGGCTGC (SEQ ID NO:15),
Vβ 13.2 GCTCAGGCTGCTGTCGGCTGC (SEQ ID NO:15),
Vβ 14 GTCTCTCGAAAAGAGAAGAGG (SEQ ID NO:16),
Vβ 15 CCCTAGAGTCTGCCATCC (SEQ ID NO:17),
Vβ 16 GGTGCAGCCTGCAGAAC (SEQ ID NO:18),
Vβ 17 GGATCCAGCAGGTAGTGCG (SEQ ID NO:19),
Vβ 18 GCAGTCAGGCCTGAGGG (SEQ ID NO:20),
Vβ 19 CACTGTGACATCGGCCCAAAAG (SEQ ID NO:21),
Vβ 20 CCTGTCCTCAGAACCGGG (SEQ ID NO:22),
Vβ 21 CCAGCCAGCAGAGCTTGG (SEQ ID NO:23),
Vβ 22 CTGAACATGAGCTCCTTGG (SEQ ID NO:24),
Vβ 23 CCGGTCCACAAAGCTGGA (SEQ ID NO:25), and
Vβ 24 CATCCGCTCACCAGGCCTG (SEQ ID NO:26), and
the second primer is Cβ AGATCTCTGCTTCTGATGGCTC (SEQ ID NO:27).

25. A method according to claim 11 wherein, in the amplifying of step (B), two first primers are employed, each of which is specific for a different variable gene segment, such that spectratypes are obtained simultaneously for two Vβ families, neither of which is a Vβ-6 family.

26. A method according to claim 12 wherein, in the amplifying of step (B), two first primers are employed, each of which is specific for a different variable gene segment, such that spectratypes are obtained simultaneously for two Vβ families, neither of which is a Vβ-6 family.

27. A method according to claim 13 wherein, in the amplifying of step (B), two first primers are employed, each of which is specific for a different variable gene segment, such that spectratypes are obtained simultaneously for two Vβ families, neither of which is a Vβ-6 family.

* * * * *